United States Patent [19]
Al-Sabah

[11] Patent Number: 5,868,723
[45] Date of Patent: Feb. 9, 1999

[54] MOISTURE SENSING AND AUDIO INDICATING APPARATUS FOR GARMENTS AND ASSOCIATED METHODS

[76] Inventor: Sabah Naser Al-Sabah, P.B. 36777 Al-Ras, 24758 Kuwait, Kuwait

[21] Appl. No.: 893,191

[22] Filed: Jul. 15, 1997

[51] Int. Cl.$^6$ .............................. G08B 21/00; A61F 5/48
[52] U.S. Cl. ..................... 604/361; 128/885; 128/886; 340/573; 340/604
[58] Field of Search ..................... 604/361; 128/885, 128/886; 340/573, 603, 604

[56] References Cited

U.S. PATENT DOCUMENTS

| | | | |
|---|---|---|---|
| 2,918,893 | 12/1959 | Norton . | |
| 3,731,685 | 5/1973 | Eidus . | |
| 3,952,746 | 4/1976 | Summers . | |
| 4,106,001 | 8/1978 | Mahoney | 340/604 |
| 4,205,672 | 6/1980 | Dvorak | 128/138 |
| 4,231,370 | 11/1980 | Mroz . | |
| 4,327,731 | 5/1982 | Powell . | |
| 4,484,573 | 11/1984 | Yoo | 128/138 |
| 4,800,370 | 1/1989 | Vetecnik | 340/573 |
| 4,977,906 | 12/1990 | Di Scipio | 128/885 |
| 5,036,859 | 8/1991 | Brown | 128/734 |
| 5,181,905 | 1/1993 | Flam | 602/41 |
| 5,258,745 | 11/1993 | Colling | 340/573 |
| 5,342,861 | 8/1994 | Raykovitz | 523/111 |
| 5,354,289 | 10/1994 | Mitchell et al. | 604/361 |
| 5,435,010 | 7/1995 | May | 2/67 |
| 5,468,236 | 11/1995 | Everhart et al. | 604/361 |
| 5,522,809 | 6/1996 | Larsonneur | 604/361 |
| 5,557,263 | 9/1996 | Fisher et al. | 340/605 |
| 5,568,128 | 10/1996 | Nair | 340/604 |
| 5,709,222 | 1/1998 | Davallou | 128/885 |
| 5,760,694 | 6/1998 | Nissim et al. | 340/604 |

*Primary Examiner*—John G. Weiss
*Assistant Examiner*—Joseph F. Weiss, Jr.
*Attorney, Agent, or Firm*—Allen, Dyer, Doppelt, Milbrath & Gilchrist, P.A.

[57] ABSTRACT

An apparatus and associated methods are provided for sensing and indicating moisture for garments such as diapers, training pants, or adult undergarments. The apparatus preferably has a sensor housing and at least one moisture sensor connected to the sensor housing for sensing moisture in a selected location of a garment. The apparatus also preferably has a separate audio indicator housing, an audible alarm sound generator positioned within the indicator housing and responsive to the at least one moisture sensor for generating an audible alarm sound, and an electroacoustic transducer responsive to the audible alarm sound generator and connected to the indicator housing for radiating acoustic power so as to audibly indicate that moisture on the garment wearer has been sensed.

24 Claims, 3 Drawing Sheets

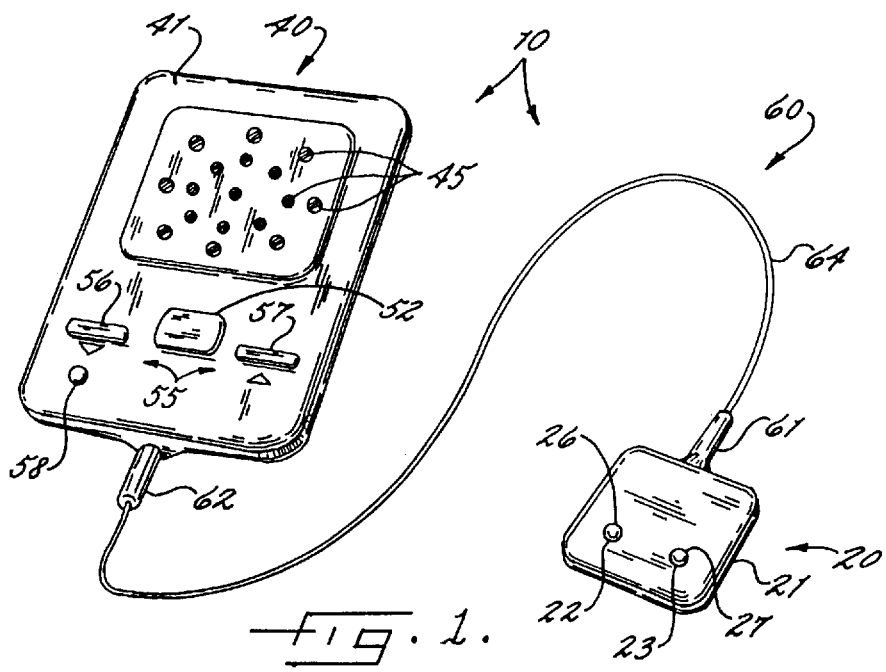
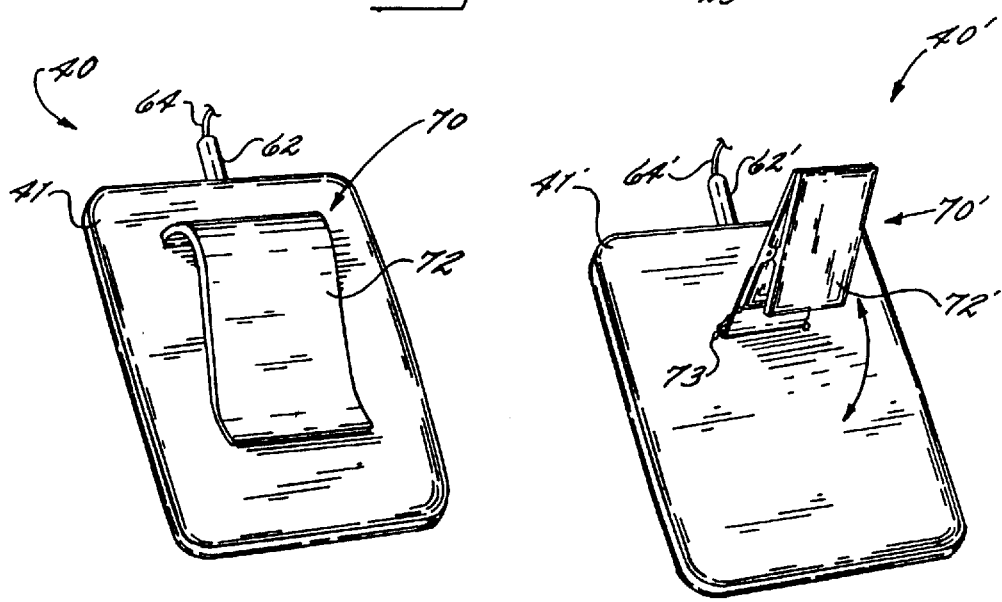
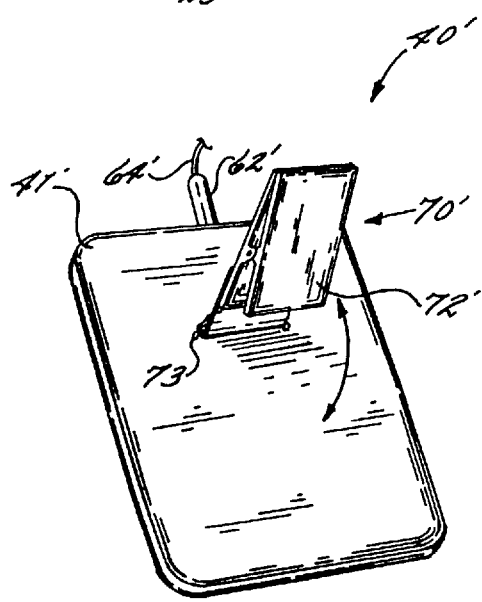

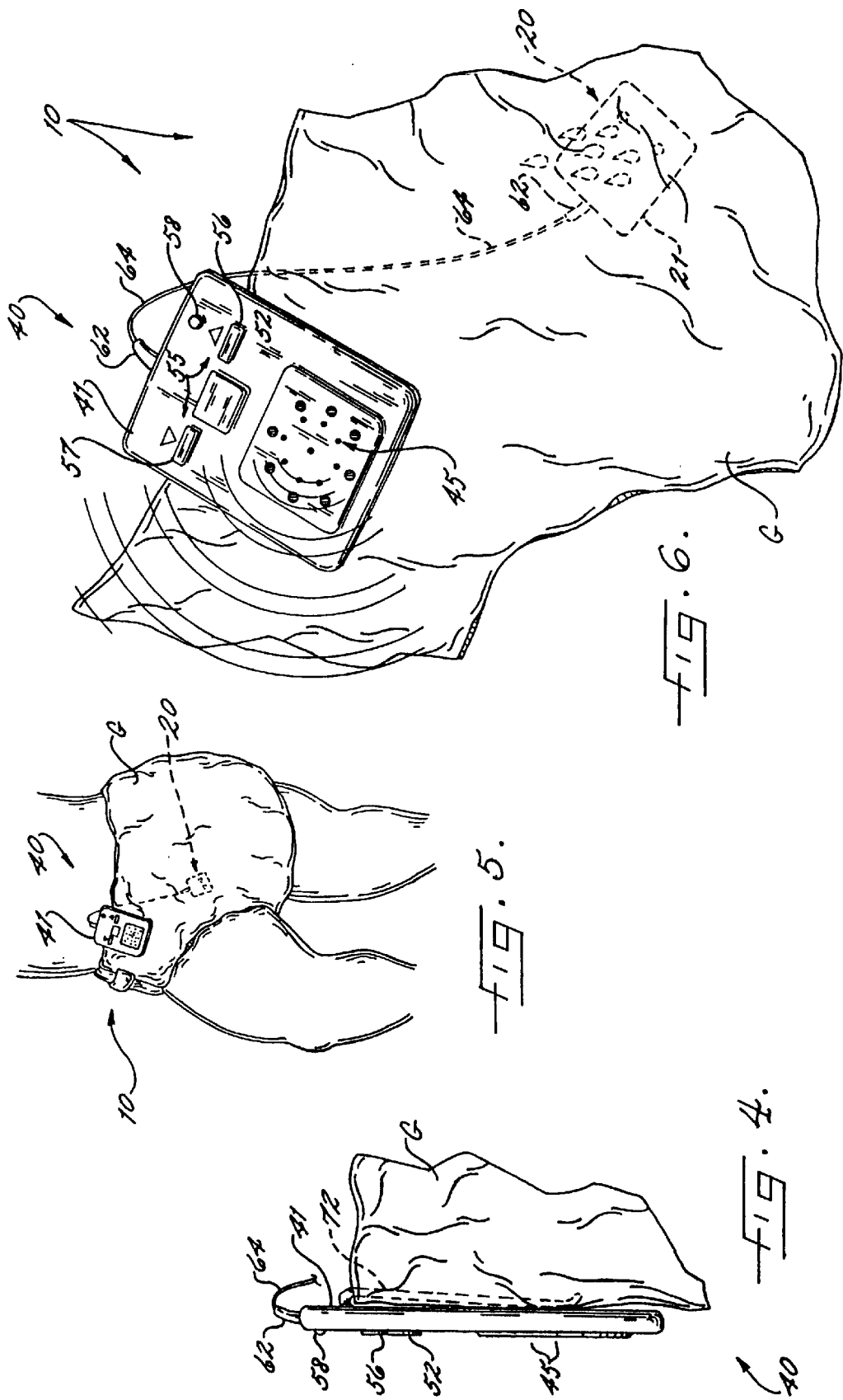

MOISTURE SENSING AND AUDIO INDICATING APPARATUS FOR GARMENTS AND ASSOCIATED METHODS

Field of the Invention

The present invention relates to the garment industry and, more particularly, to moisture indicators in the diaper, training pant, and adult undergarment industries.

Background of the Invention

Children and adult diaper industries have grown significantly over the years, especially the disposable diaper industries. These diaper have included various shapes, sizes, and features which are designed to be beneficial to the various users thereof. For example, moisture superabsorption and non-leaking features, especially around the legs of diapers, has become both beneficial to the users of the diapers and commercially successful for the manufacturers of diapers.

Nevertheless, one problem has continued to be underemphasized in this industry: How can a parent or guardian of a child or an adult readily discern whether the child or adult is wet? The conventional method for both disposable and re-usable diapers previously has been for the parent or guardian to feel the inside of a diaper with their fingers to determine if moisture is present. This conventional moisture sensing method, however, is unpleasant, can be quite unsanitary, and requires cleaning of the parent's or guardian's fingers.

To address this problem, diapers have been developed which have moisture or wetness indicating portions manufactured integral with or built-in the diaper itself. Examples of some of these diapers can be seen in U.S. Pat. No. 3,952,746 by Summers titled "Humidity Indicating Diaper Cover," U.S. Pat. No. 4,231,370 by Mroz et al. titled "Disposable Diaper Type Garment Having Wetness Indicator," U.S. Pat. No. 5,468,236 by Everhart et al. titled "Disposable Absorbent Product Incorporating Chemically Reactive Substance," and U.S. Pat. No. 5,522,809 by Larsonneur titled "Absorbent Adult Fitted Briefs And Pads." As seen in U.S. Pat. No. 5,354,289 by Mitchell et al. titled "Absorbent Product Including Super Absorbent Material And A Fluid Absorption Capacity Monitor," these built-in wetness indicators for diapers have even been developed to the extent of assisting a parent or guardian on determining how much or the capacity to which the diaper has already absorbed moisture or wetness.

These built-in wetness indicators, however, cannot be readily used with non-disposable diapers, can significantly increase the cost of the disposable diaper to the end user, and require a visual indication of wetness, e.g., in other words, the parent or guardian has to be observing or visually monitoring the wearer of the diaper. Also, because these built-in wetness indicators are often used with the superabsorbency properties of disposable diapers, these indicators can often provide a parent or guardian a false sense of security about the wetness of the wearer of the diaper. When a parent or guardian has this false sense of security, a diaper having super absorbency qualities with such a wetness indicator, for example, can lead to skin irritations or spillage when a diaper particularly full of wetness is being removed. These are two problems, however, which were originally trying to be avoided.

Additionally, spray or hot melt adhesives for the diaper industry which change colors to indicate wetness have also been developed. An example of a spray or hot melt adhesive of this type can be seen in U.S. Pat. No. 5,341,861 by Raykovitz titled "Hot Melt Wetness Indicator". These spray or hot melt adhesives, however, are also used in the manufacture of the diaper itself. Accordingly, these diapers can also experience many of the same problems associated with built-in wetness indicators as described above.

Further, it has been known to provide a moisture sensing strip of gauze-like material for sensing moisture in diapers and surgical dressings. An example of this gauze-like moisture sensing strip can be seen in U.S. Pat. No. 3,731,685 by Eidus titled "3,731,685." Because the previous moisture sensing strip has been formed of a gauze-like material, however, this moisture sensing strip can still be quite expensive to manufacture, can be difficult and expensive to package for the end users, and provides only a visual indication to the parent or guardian that wetness or sensing of moisture has occurred.

Summary of the Invention

In view of the foregoing, the present invention advantageously provides a moisture sensing and audio indicating apparatus and associated methods which are readily adapted for use with re-usable and disposable diapers, training pants, or other children and adult undergarments. The present invention also advantageously provides a compact, portable, and light-weight audio moisture sensing indicator which readily attaches and detaches from re-usable and disposable diapers, training pants, or other children and adult undergarments. The present invention additionally provides a moisture sensing and audio indicating apparatus which allows a user to advantageously control whether or not the audible alarm is used, the volume of the alarm, and at least one status indication regarding the operation of the indicator. The present invention further advantageously provides an apparatus for sensing and indicating moisture for garments which includes moisture sensing means adapted to be positioned within a garment of a wearer for sensing moisture in a selected location of the garment and audio indicating means responsive to the moisture sensing means and adapted to be connected to the garment for audibly indicating the sensing of moisture in the selected location of the garment.

More particularly, an apparatus for sensing and indicating moisture for garments according to the present invention preferably includes moisture sensing means adapted to be positioned within inner confines of a garment of a wearer for sensing moisture in a selected location of the garment. The moisture sensing means includes a sensor housing and at least one moisture sensor connected to the sensor housing. The apparatus also includes audio indicating means connected to the moisture sensing means and adapted to be detachably connected to the garment for audibly indicating the sensing of moisture in the selected location of the garment. The audio indicating means preferably includes a separate audio indicator housing, an audible alarm sound generator positioned within the indicator housing and responsive to the moisture sensor for generating an audible alarm sound, and an electroacoustic transducer responsive to the audible alarm sound generator and connected to the indicator housing for radiating acoustic power so as to audibly indicate that moisture on the garment wearer has been sensed.

According to another aspect of the present invention, the audio indicating means of the apparatus for sensing and indicating moisture for garments preferably also includes audio indicating controlling means connected to the indicator housing for operationally controlling the audio indicating means. The audio indicating controlling means includes alarm activating means connected to the indicator housing and responsive to a user for activating the at least one moisture sensor and the audio alarm sound generator to thereby indicate an alarm condition responsive to the sensing of moisture. The audio indicating means further preferably includes a power source, e.g., a battery, positioned within the indicator housing, and the alarm activating means preferably includes an alarm switch connected to the indicator housing and the power source for switching power from the power source to the moisture sensor and the audio alarm sound generator. The indicating controlling means preferably also includes audio level controlling means connected to the indicator housing and responsive to a user for controlling the audio level of the audio alarm sound generator and status displaying means connected to the indicator housing for displaying at least one status of the audio indicating means.

The present invention also advantageously provides methods of sensing and indicating moisture for garments. A method preferably includes sensing moisture in a selected location of a garment and audibly indicating the sensing of the moisture in the selected location of the garment. Another method preferably includes positioning a moisture sensor within the inner confines of a garment and detachably connecting an audio alarm indicator responsive to the moisture sensor to a garment. Moisture is then sensed by the moisture sensor and the alarm indicator responsively audibly indicates the sensing of the moisture.

Because an apparatus for sensing moisture and audibly indicating that moisture has been sensed is preferably provided by an audio alarm moisture sensing indicator that has two flexibly connected portions, e.g., a moisture sensing portion and an audio alarm indicating portion, the moisture sensing portion can advantageously be positioned in numerous locations within the inner confines of a diaper, training pant, or adult undergarment so that moisture can readily be sensed in the selected location. The audio alarm indicating portion, for example, can be readily attached to a peripheral edge of the diaper, training pant, or adult undergarment for providing an audio alarm to a parent, guardian, or the like. In this manner, the infant, child, or adult does not require continual visual observance to discover whether or not the wearer is wet. The apparatus and methods of the present invention can readily be used, for example, by workers in nurseries, nursing homes, hospitals, day care centers, or homes to more easily manage the care of infants, children, or adults. The apparatus of the present invention advantageously can be reused numerous times so that re-usable diapers or other undergarments and less expensive disposable diapers, training pants, and other disposable garments can be used instead of garments with built-in moisture indicators which can only be used one time before disposal.

Brief Description of the Drawings

Some of the features, advantages, and benefits of the present invention having been stated, others will become apparent as the description proceeds when taken in conjunction with the accompanying drawings in which:

FIG. 1 is a front perspective view of a moisture sensing and audio indicating apparatus for garments according to the present invention;

FIG. 2 is a rear perspective view of a moisture sensing and audio indicating apparatus for garments according to a first embodiment of the present invention;

FIG. 3 is a rear perspective view of a moisture sensing and audio indicating apparatus for garments according to a second embodiment of the present invention;

FIG. 4 is a fragmentary side elevational view illustrating a moisture sensing and audio indicating apparatus mounted to a diaper according to a first embodiment of the present invention;

FIG. 5 is a perspective view of a moisture sensing and audio indicating apparatus mounted to a diaper according to a first embodiment of the first invention;

FIG. 6 is an enlarged perspective view of a moisture sensing and audio indicating apparatus for garments illustrating the sensing of moisture in phantom view and the emission of an audio sound therefrom according to a first embodiment of the present invention.

Detailed Description of Preferred Embodiments

Figure 7:
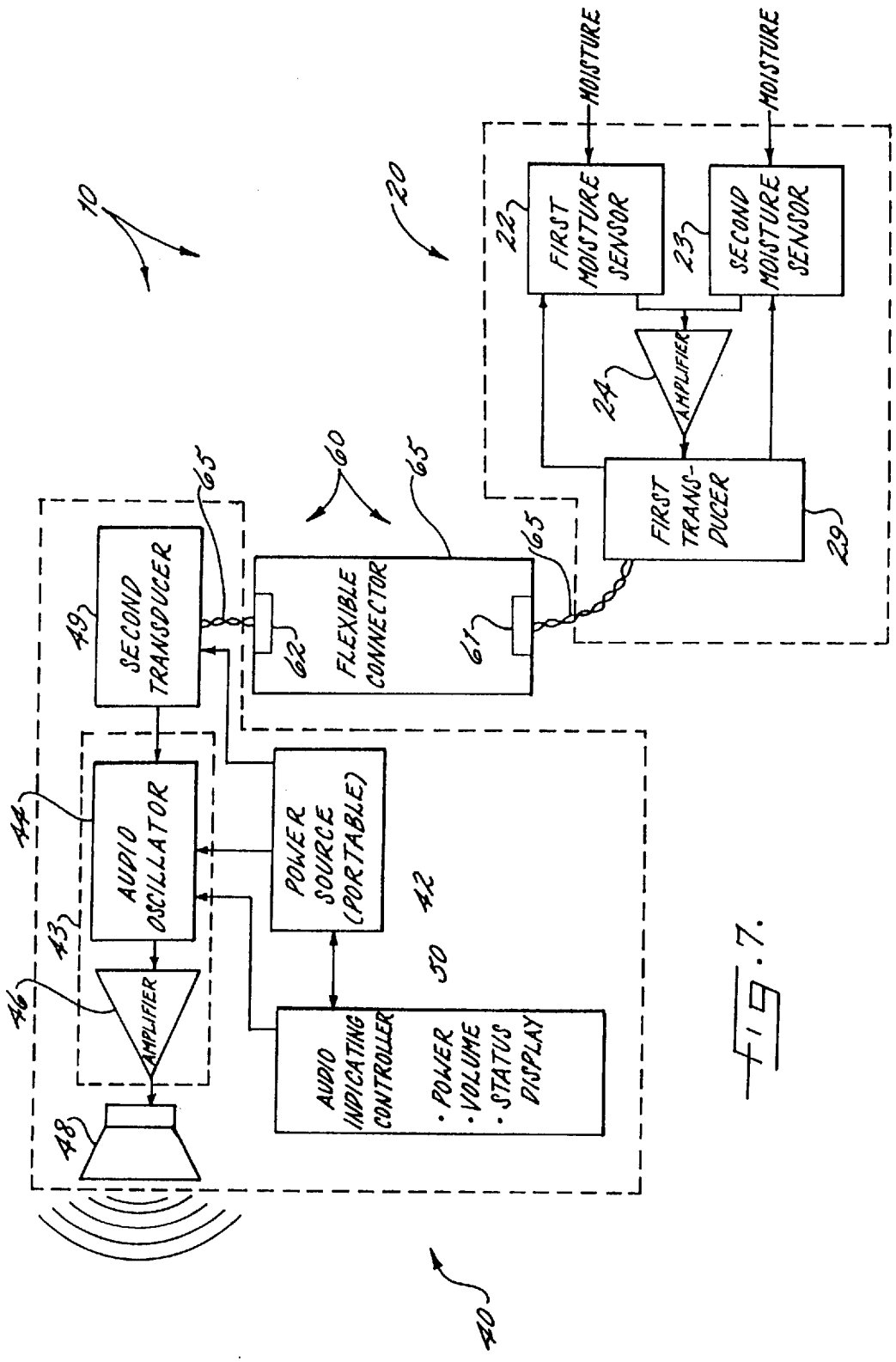
FIG. 7 is a schematic block diagram of a moisture sensing and audio indicating apparatus for garments according to the present invention.

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime notation is used to indicate similar elements in alternative embodiments.

FIGS. 1 and 5–7 illustrate an apparatus 10 for sensing and audibly indicating moisture for garments according to the present invention. The apparatus 10 preferably includes moisture sensing means 20 adapted to be positioned within a garment of a wearer for sensing moisture in a selected location of the garment G. The garment G is preferably a diaper, but other garments such as a child training pant, an adult disposable pant, or other undergarments can also advantageously be used therewith according to the present invention. The moisture sensing means 20 preferably includes a sensor housing 21 formed of a plastic material and at least one moisture sensor, e.g., preferably a pair of moisture sensors 22, 23, connected to the sensor housing 21. The moisture sensors 22, 23 preferably are mounted within the sensor housing 21 so that moisture can be sensed through a pair of respective openings 26, 27 in the housing 21. As understood by those skilled in the art, the moisture sensors 22, 23, for example, can be sensing circuits which detect a change in impedance of a plastic material absorbing moisture or which detect a change in the surface impedance, i.e., resistance and capacitance, of insulators with closely spaced electrodes. The detected change in impedance preferably produces an electrical signal which is preferably amplified by a sensing amplifier 24. These sensing circuits preferably operate on low power so that the apparatus 10 operate over an extended period of time without replacing or recharging a power source 42 for the apparatus 10.

The apparatus 10 also preferably includes audio indicating means 40 connected to the moisture sensing means 20 and adapted to be detachably connected to the garment G for audibly indicating the sensing of moisture in the selected location of the garment G (see FIGS. 6–7). The audio indicating means 40 preferably has a separate audio indicator housing 41 also formed of a plastic material and a power source 42 positioned within the indicator housing 41. The power source 42 is preferably provided by at least one portable battery which supplies direct current power to the electronic circuit of the apparatus 10. An audible alarm sound generator 43 is connected to the power source 42, positioned within the indicator housing 41, and responsive to the moisture sensors 22, 23 for generating an audible alarm sound. The audible alarm sound generator preferably includes a piezoelectric audio oscillator 44 and an amplifier 46 connected to the oscillator 44 for amplifying the generated audible alarm sound. An electroacoustic transducer, e.g., a loudspeaker 48, is connected to the amplifier 46 and to the indicator housing 41 for radiating acoustic power so as to audibly indicate that moisture on the garment wearer has been sensed. The indicator housing 21 preferably has a plurality of openings 45 formed on a front surface thereof. The loudspeaker is preferably positioned for radiating acoustic power through the plurality of openings 45 in the indicator housing 41 (see FIG. 6).

The apparatus 10 also preferably has flexible connecting means 60 respectively connected to the sensor housing 21 and to the separate indicator housing 41 for flexibly connecting the sensor housing 21 to the separate indicator housing 41 to thereby allow the plurality of moisture sensors 22, 23 to readily electrically communicate with the audible alarm sound generator 43. The flexible connecting means 60 is preferably provided by a pair of connectors 61, 62 respectively connected to the sensor housing 21 and to the indicator housing 41. The flexible connecting means 60 also has an elongate and flexible sheath 64 formed of a plastic material having respective ends thereof connected to the pair of connectors 61, 62. The flexible connecting means 60 further preferably has wire 65 or cable, such as twisted pair wires, electrically connected to the pair of connectors 61, 62 and positioned within the flexible sheath 64. The pair of connectors 61, 62 preferably provide an electrical connection to a first transducer 29 positioned within the sensor housing 21 and to a second transducer 49 positioned within the indicator housing 41. As understood by those skilled in the art, each of the first and second transducers 29, 49, for example, can be a connector interface positioned within each housing 21, 41, a transceiver, or an input output/circuit.

As perhaps best illustrated in FIGS. 1 and 6–7, the audio indicating means 40 further includes audio indicating controlling means 50 connected to the indicator housing 41 and to the power source 42 for operationally controlling the audio indicating means 40. The audio indicating controlling means 50 preferably includes alarm activating means connected to the indicator housing 41 and responsive to a user for activating the plurality of moisture sensors 22, 23 and the audio alarm sound generator 43 to thereby indicate an alarm condition responsive to the sensing of moisture by at least one of the plurality of moisture sensors 22, 23. The alarm activating means is preferably provided by an alarm switch 52 connected to the indicator housing 41 and the power source 42 for operationally switching power from the power source 42 to the moisture sensors 22, 23 and the audio alarm sound generator 43.

The audio indicating controlling means 50 preferably also includes audio level controlling means 55 connected to the indicator housing 41 and responsive to a user for controlling the audio level of the audio alarm sound generator 43. The audio level controlling means 55 preferably includes a pair of manually operated volume control switches 56, 57 connected to a front surface of the indicator housing 41 for controlling the volume of the alarm, e.g., louder or quieter. The audio indicating controlling means 50 further preferably includes status displaying means connected to the indicator housing 41 for visually displaying at least one status of the audio indicating means 40. The status displaying means is preferably provided by at least one light indicator 58, e.g., a lamp, responsive to the power source 42 for indicating a low power state representative of the low amount of power in the power source 42, e.g., batteries.

As illustrated in the first and second embodiments of FIGS. 2–4 the apparatus 10 further includes garment fastening means 70, 70' connected to the indicator housing 41, 41' of the audio indicating means 40, 40' for detachably fastening the indicator housing 41, 41' to a garment G. The garment fastening means 70 according to a first embodiment of the present invention preferably has a flexible clip 72 connected to the indicator housing 41 for clippingly attaching the indicator housing 41 to a peripheral edge of the garment G (see FIGS. 2 and 4). The clip 72, for example, can integrally formed of a plastic material as a single piece with the indicator housing 41 during the molding of the housing 41. The garment fastening means 70' according to a second embodiment of the present invention preferably has a flexible clip 72' pivotally connected to the indicator housing 41' for flexibly clippingly attaching the indicator housing 41' in a plurality of positions to the garment G (see FIG. 3). The flexible clip 72' of this embodiment is preferably slidably attached to a retainer 73 connected to the housing 41' and connected along an end of the clip 72' so that the clip 72' can advantageously pivot within about 180 degrees, as indicated by the arrows, for mounting to a garment G n various positions.

As illustrated in FIGS. 1–7, and as described above herein, the present invention also advantageously provides methods of sensing and indicating moisture for garments G. A method preferably includes sensing moisture in a selected location of a garment G and audibly indicating the sensing of the moisture in the selected location of the garment G. The audibly indicating step preferably includes generating an audible alarm sound, amplifying the alarm sound, and radiating acoustic power so as to audibly indicate that moisture on the garment wearer has been sensed.

The method can also include controlling the audible alarm sound. The controlling step preferably includes activating at least one moisture sensor 22, 23 and an audio alarm sound generator 43 responsive to a user to thereby indicate an alarm condition responsive to the sensing of the moisture. The controlling step further includes controlling the audio level of the audio alarm sound generator 43 and displaying at least one status of an alarm condition. The at least one status of an alarm condition preferably is a visual indication a low power state representative of the low amount of power in a portable power source 42. The method can further include detachably fastening an audio alarm indicator housing 41 to the garment G.

Another method of sensing and indicating moisture for garments G preferably includes positioning a moisture sensor 22, 23 within the inner confines of a garment G and detachably connecting an audio alarm indicator 40 responsive to the moisture sensor 22, 23 to a garment G. Moisture is then sensed by the moisture sensor 22, 23 and the alarm indicator 40 responsively audibly indicates the sensing of the moisture. The audibly indicating step preferably includes generating an audible alarm sound, amplifying the alarm sound, and radiating acoustic power so as to audibly indicate that moisture on the garment wearer has been sensed.

The method can also include controlling the audible alarm sound. The controlling step preferably includes activating the moisture sensor 22, 23 and the alarm indicator 40 responsive to a user to thereby indicate an alarm condition responsive to the sensing of the moisture. The controlling step further includes controlling the audio level of the audio indicator 40 and displaying at least one status of an alarm condition. The at least one status of an alarm condition preferably is a visual indication a low power state representative of the low amount of power in a portable power source 42.

Because an apparatus 10 for sensing moisture and audibly indicating that moisture has been sensed is preferably provided by an audio alarm moisture sensing indicator that has two flexibly connected portions, e.g., a moisture sensing portion 20 and an audio alarm indicating portion 40, the moisture sensing portion 20 can advantageously be positioned in numerous locations within the inner confines of a diaper, training pant, or adult undergarment so that moisture can readily be sensed in the selected location. The audio alarm indicating portion 40, for example, can be readily attached to a peripheral edge of the diaper, training pant, or adult undergarment for providing an audio alarm to a parent, guardian, or the like. In this manner, the infant, child, or adult does not require continual visual observance to discover whether or not the wearer is wet. The apparatus 10 and associated methods of the present invention can readily be used, for example, by workers in nurseries, nursing homes, hospitals, day care centers, or homes to more easily manage the care of infants, children, or adults. The apparatus 10 of the present invention advantageously can be reused numerous times so that re-usable diapers or other undergarments and less expensive disposable diapers, training pants, and other disposable garments can be used instead of garments, e.g., diapers, with built-in moisture indicators which can only be used one time before disposal.

In the drawings and specification, there have been disclosed typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. An apparatus for sensing and indicating moisture for garments, the apparatus comprising:

moisture sensing means adapted to be positioned within inner confines of a garment of a wearer for sensing moisture in a selected location of the garment, said moisture sensing means including a sensor housing, at least one opening formed in said housing and at least one moisture sensor positioned within said at least one opening of said sensor housing; and audio indicating means connected to said moisture sensing means and adapted to be detachably connected to the garment for audibly indicating the sensing of moisture in the selected location of the garment, said audio indicating means including a separate audio indicator housing, an audible alarm sound generator positioned within said indicator housing and responsive to said at least one moisture sensor for generating an audible alarm sound, an electroacoustic transducer responsive to said audible alarm sound generator and connected to said indicator housing for radiating acoustic power so as to audibly indicate that moisture on the garment wearer has been sensed, and audio indicating controlling means connected to said indicator housing for controlling said audio indicating means; and flexible connecting means respectively connected to said sensor housing and to said separate indicator housing for flexibly connecting said sensor housing to said separate indicator housing to thereby allow said at least one moisture sensor to readily electrically communicate with said audible alarm sound generator.

2. An apparatus as defined in claim 1, wherein said audio indicating controlling means includes alarm activating means connected to said indicator housing and responsive to a user for activating said at least one moisture sensor and said audio alarm sound generator to thereby indicate an alarm condition responsive to the sensing of moisture.

3. An apparatus as defined in claim 2, wherein said audio indicating means further includes a power source associated with said indicator housing, and wherein said alarm activating means includes an alarm switch connected to said indicator housing and said power source for switching power from said power source to said moisture sensor and said audio alarm sound generator.

4. An apparatus as defined in claim 1, wherein said audio indicating controlling means includes audio level controlling means connected to said indicator housing and responsive to a user for controlling the audio level of said audio alarm sound generator.

5. An apparatus as defined in claim 2, wherein said audio indicating controlling means includes status displaying means connected to said indicator housing for displaying at least one status of said audio indicating means.

6. An apparatus as defined in claim 5, wherein said audio indicating means further includes a power source positioned within said indicator housing for supplying power, and wherein said status displaying means comprises a light indicator responsive to said power source for indicating a low power state representative of the low amount of power in said power source.

7. An apparatus as defined in claim 1, further comprising garment fastening means connected to said indicator housing of said audio indicating means for detachably fastening said indicator housing to a garment.

8. An apparatus as defined in claim 1, wherein said indicator housing includes a plurality of openings formed therein, and wherein said electroacoustic transducer comprises a loudspeaker positioned for radiating acoustic power through said plurality of openings.

9. An apparatus for sensing and indicating moisture for garments, the apparatus comprising:

moisture sensing means adapted to be positioned within a garment of a wearer for sensing moisture in a selected location of the garment, said moisture sensing means including a sensor housing, at least one opening formed in said sensor housing, and at least one moisture sensor positioned within said at least one opening of said sensor housing; and audio indicating means connected to said moisture sensing means and adapted to be detachably connected to the garment for audibly indicating the sensing of moisture in the selected location of the garment, said audio indicating means including a separate audio indicator housing, a power source positioned within said indicator housing, an audible alarm sound generator connected to said power source, positioned within said indicator housing, and responsive to said at least one moisture sensor for generating an audible alarm sound, an electroacoustic transducer responsive to said audible alarm sound generator and connected to said indicator housing for radiating acoustic power so as to audibly indicate that moisture on the garment wearer has been sensed, and audio indicating controlling means connected to said indicator housing for controlling said audio indicating means; and flexible connecting means respectively connected to said sensor housing and to said separate audio indicator housing for flexibly connecting said sensor housing to said separate audio indicator housing to thereby allow said at least one moisture sensor to readily electrically communicate with said audible alarm sound generator.

10. An apparatus as defined in claim 9, wherein said at least one opening of said sensor housing comprises a plurality of openings, wherein said at least one moisture sensor comprises a plurality of moisture sensors each positioned within only one of the plurality of openings of said sensor housing, and wherein said audio indicating controlling means includes alarm activating means connected to said indicator housing and responsive to a user for activating said plurality of moisture sensors and said audio alarm sound generator to thereby indicate an alarm condition responsive to the sensing of moisture by at least one of said plurality of moisture sensors.

11. An apparatus as defined in claim 10 wherein said power source comprises at least one battery, and wherein said alarm activating means includes an alarm switch connected to said indicator housing and said at least one battery for switching power from said at least one battery to said moisture sensor and said audio alarm sound generator.

12. An apparatus as defined in claim 11, wherein said audio indicating controlling means includes audio level controlling means connected to said indicator housing and responsive to a user for controlling the audio level of said audio alarm sound generator.

13. An apparatus as defined in claim 12, wherein said audio indicating controlling means includes status displaying means connected to said indicator housing for visually displaying at least one status of said audio indicating means.

14. An apparatus as defined in claim 13, wherein said status displaying means comprises a lamp responsive to said at least one battery for indicating a low power state representative of the low amount of power in said at least one battery.

15. An apparatus as defined in claim 14, wherein said indicator housing includes a plurality of openings formed therein, and wherein said electroacoustic transducer comprises a loudspeaker positioned for radiating acoustic power through said plurality of openings.

16. An apparatus as defined in claim 15, further comprising garment fastening means connected to said indicator housing of said audio indicating means for detachably fastening said indicator housing to a garment, said garment fastening means comprising a flexible clip pivotally connected to said indicator housing for flexibly clippingly attaching said indicator housing in a plurality of positions to the garment.

17. An apparatus as defined in claim 15, further comprising garment fastening means connected to said indicator housing of said audio indicating means for detachably fastening said indicator housing to a garment, said garment fastening means comprising a flexible clip connected to said indicator housing for clippingly attaching said indicator housing to a peripheral edge of the garment.

18. A method of sensing and indicating moisture for garments, the method comprising:

positioning at least one moisture sensor within the inner confines of a garment, the at least one moisture sensor being positioned within at least one opening of a sensor housing;

detachably connecting an audio alarm indicator to a garment, the audio alarm indicator having a separate audio indicator housing, an audio alarm sound generator positioned within the indicator housing for generating an audible alarm sound, and an audio indicating controller connected to the indicator housing for controlling the audio indicator and being flexibly connected by a flexible connector to the sensor housing, and being responsive to at least one moisture sensor;

sensing moisture in the garment responsive to the at least one moisture sensor; and audibly indicating the sensing of the moisture in the garment by the audio alarm indicator.

19. A method as defined in claim 18, wherein the audibly indicating step includes generating an audible alarm sound, amplifying the alarm sound, and radiating acoustic power so as to audibly indicate that moisture on the garment wearer has been sensed.

20. A method as defined in claim 19, further comprising controlling the audio alarm indicator by the audio indicating controller connected thereto.

21. A method as defined in claim 20, wherein the controlling step includes manually activating the at least one moisture sensor and the audio alarm sound generator responsive to a user to thereby indicate an alarm condition responsive to the sensing of the moisture.

22. A method as defined in claim 21, wherein the controlling step further includes controlling the audio level of the audio alarm sound generator.

23. A method as defined in claim 22, wherein the controlling step further includes displaying at least one status of an alarm condition.

24. A method as defined in claim 23, wherein the at least one status of an alarm condition comprises indicating a low power state representative of the low amount of power in a power source.

* * * * *